United States Patent
Stapela et al.

(10) Patent No.: US 12,338,207 B2
(45) Date of Patent: Jun. 24, 2025

(54) PYROLYSIS OF CARBON BASED MATERIAL

(71) Applicant: MICROWAVE SOLUTIONS GMBH, Riehen (CH)

(72) Inventors: Annelie Stapela, Riehen (CH); Mathys Johannes Rossouw, Rayton Gauteng (ZA)

(73) Assignee: MICROWAVE SOLUTIONS GMBH, Riehen (CH)

( * ) Notice: Subject to any disclaimer, the term of this patent is extended or adjusted under 35 U.S.C. 154(b) by 99 days.

(21) Appl. No.: 18/026,450

(22) PCT Filed: Sep. 16, 2021

(86) PCT No.: PCT/EP2021/075539
§ 371 (c)(1),
(2) Date: Mar. 15, 2023

(87) PCT Pub. No.: WO2022/058457
PCT Pub. Date: Mar. 24, 2022

(65) Prior Publication Data
US 2023/0257324 A1    Aug. 17, 2023

(30) Foreign Application Priority Data
Sep. 18, 2020   (CH) .................................... 01182/20

(51) Int. Cl.
*C07C 4/04*        (2006.01)
*C08J 11/12*       (2006.01)
(Continued)

(52) U.S. Cl.
CPC ................. *C07C 4/04* (2013.01); *C08J 11/12* (2013.01); *C10B 53/07* (2013.01); *C10G 1/10* (2013.01);
(Continued)

(58) Field of Classification Search
CPC ......... C07C 4/04; C08J 11/12; C08J 2321/00; C08J 2387/00; C08J 2317/00;
(Continued)

(56) References Cited

U.S. PATENT DOCUMENTS

| 5,084,141 A | 1/1992 | Holland |
| 2007/0102279 A1 | 5/2007 | Novak |

FOREIGN PATENT DOCUMENTS

| WO | 2010079408 A1 | 7/2010 |

OTHER PUBLICATIONS

Undri Andrea et al: "Upgraded fuel from microwave assisted pyrolysis of waste tire", Fuel, IPC Sience and Technology Press, Guildford, GB, vol. 115, Aug. 1, 2013 (Aug. 1, 2013), pp. 600-608, XP028735451, ISSN: 0016-2361, DOI: 10.1016/J.FUEL.2013.07.058, p. 601; figure 1, p. 602, paragraph 3.1, abstract; figures; examples; tables.
(Continued)

*Primary Examiner* — Thuan D Dang
(74) *Attorney, Agent, or Firm* — Eschweiler & Potashnik, LLC

(57) ABSTRACT

The invention relates to a pyrolysis method and reactor for recovering at least one component from a carbon based material using thermal decomposition. The carbon based material is delivered to a pyrolytic chamber (1), exposed to a controlled atmosphere and heated to a decomposition temperature of the at least one component in the pyrolytic chamber (1) by microwave radiation. A variable power microwave radiation at frequencies between 300 MHz and 2200 MHZ is applied to sequentially increase a temperature in the pyrolytic chamber (1) over a temperature range including the decomposition temperature of the at least one component.

17 Claims, 1 Drawing Sheet

Figure 1:
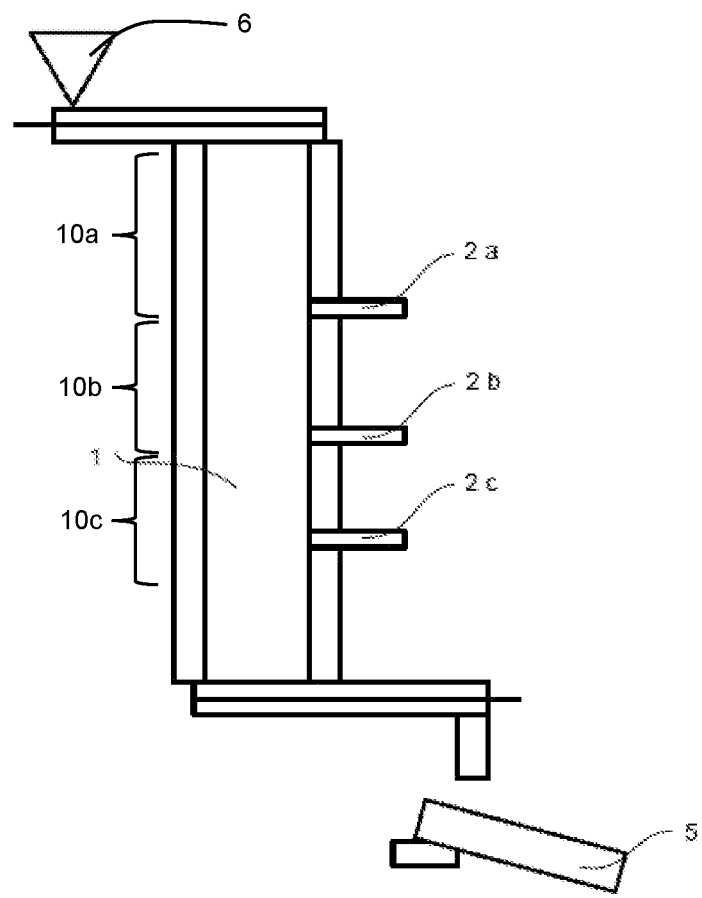

(51) Int. Cl.
 *C10B 53/07* (2006.01)
 *C10G 1/10* (2006.01)
(52) U.S. Cl.
 CPC ........ *C08J 2321/00* (2013.01); *C08J 2387/00* (2013.01); *C10G 2300/1003* (2013.01); *C10G 2400/20* (2013.01); *C10G 2400/30* (2013.01)
(58) Field of Classification Search
 CPC ........ C08J 2319/00; C10B 53/07; C10G 1/10; C10G 2300/1003; C10G 2400/20; C10G 2400/30; C10G 1/00; Y02P 20/143; B01J 19/126
 See application file for complete search history.

(56) References Cited

OTHER PUBLICATIONS

Czajczynska D. et al: "Potential of pyrolysis processes in the waste management sector" Thermal Science and Engineering Progress, vol. 3, Sep. 1, 2017 (Sep. 1, 2017), pp. 171-197, XP055850950, ISSN: 2451-9049, DOI: 10.1016/j.tsep.2017.06.003; paragraphs [02.5], [03.4], [3.4.1], p. 174, left-hand column paragraph first.
PCT Search Report and Written Opinion dated Dec. 20, 2021 in connection with PCT Application No. PCT/EP2021/075539.

PYROLYSIS OF CARBON BASED MATERIAL

CROSS-REFERENCE TO RELATED APPLICATIONS

This application is a National Phase entry application of International Patent Application No. PCT/EP2021/075539 filed Sep. 16, 2021, claims the benefit of priority to Foreign (Switzerland) Patent Application No. 01182/20, filed Sep. 18, 2020. These prior applications are incorporated herein by reference.

The invention relates to a pyrolysis method and a pyrolysis reactor for extracting or recovering compounds from carbon based materials. Particularly, the invention relates to the recovery of pyrolitical oils, hydrocarbons, monomers and chemicals, especially from feedstock and waste streams such as tires, plastics, rubber products and polymer composites.

Carbon based materials like tires, plastics, rubber products and polymer composites, which are used in a broad variety of products, constructions and manufacturing processes, represent a source of energy and raw material at the end of life of the products and constructions. Also, scrap materials accruing from manufacturing and production processes using such materials represent sources of energy and raw material. To support a circular economy these resources should be recovered and redirected into product manufacturing and construction.

For example, efforts to recycle tires using microwave technology have been described in U.S. Pat. No. 5,507,927. Tires are fed into a microwave chamber as a tire waste stream and are exposed to a reduction atmosphere and microwave radiation. The temperature of the tires is monitored and a power input to the microwave generators is adjusted as required to obtain optimum temperature for reducing the tire material. The chamber is kept at slightly above atmospheric pressure to facilitate removal of gaseous products. Further, the reduction atmosphere is adjusted by increasing the concentration of reducing gases as the tire material breaks down. For reducing the tire material, twelve magnetrons are used, wherein each of them has 1.5 kW of power at a wavelength of 2450 MHZ.

Efforts to decompose plastics, which is not itself susceptible to microwave heating, have been described in U.S. Pat. No. 5,084,140. The plastics is mixed with carbonaceous material, such as waste tire material, and subjected to microwave radiation to heat the plastics to 400° C. to 800° C. and cause pyrolysis of the plastics.

In summary, the prior work has involved the use of single-frequency microwave radiation and high frequency systems for recovering specific compounds from waste materials. However, high frequency microwave systems have a low microwave energy penetration into a material to be treated. Further, microwave energy at a frequency of 2.45 GHZ is derived from electrical energy with a conversion efficiency of approximately only 50% for 2.45 GHz. The use of multiple small magnetrons in a pyrolysis reactor, that are shut on and off for temperature control, is inefficient and the temperature control is not very precise. Especially, pyrolitical oils, hydrocarbons, monomers and chemicals are very temperature sensitive resulting in yield and quality of the recovered compounds being affected negatively.

It is an object of the invention to provide a pyrolysis process and a pyrolysis reactor that improve the yield and quality of compounds recovered from carbon based materials, allow for high volumes of carbon based materials to be processed, and enhance economic and commercial viability of compounds recovered from carbon based materials.

These and other objects, which will appear from the description below, are achieved by a pyrolysis method and a pyrolysis reactor for recovering at least one component from a carbon based material using thermal decomposition as set forth in the appended independent claims. Preferred embodiments are defined in dependent claims.

According to the present invention the carbon based material is treated by the pyrolysis method by delivering the material to a pyrolytic chamber. In the chamber the carbon based material is exposed to a controlled atmosphere and heated to a decomposition temperature of at least one component of the carbon based material. Heating is accomplished by a variable power microwave radiation at frequencies between 300 MHz and 2200 MHZ to sequentially vary a temperature in the pyrolytic chamber over a temperature range including the decomposition temperature of the at least one component. Particularly the temperature in the pyrolytic chamber can be increased in successive heating steps for applying different decomposition temperatures to the carbon based material and recovering differing components.

The pyrolysis reactor for recovering at least one component from the carbon based material according to the present invention comprises a pyrolytic chamber for accommodating the carbon based material and at least one microwave radiation source as a heat source for heating the carbon based material to a decomposition temperature of the carbon based material. Further, a control unit is provided, which comprises a microwave radiation control for applying variable power of microwave radiation at frequencies between 300 MHz and 2200 MHZ to the carbon based material, and a temperature control controlling a sequentially varying or increasing decomposition temperature of the carbon based material.

Advantageously, the temperature in the pyrolytic chamber does not exceed 750° C.

The variable power microwave radiation is generated by the at least one microwave radiation that preferably provides a continuously changeable radiation power. Thus, the microwave radiation and the temperature in the pyrolytic chamber, respectively, are not simply altered in rather discrete or incremental steps for example by switching on and off magnetrons as known from the prior art. Advantageously, the microwave radiation comprises one or more radiation frequencies between 300 MHz and 2.2 GHz. The applied microwave radiation and chamber temperature can be adjusted in a precise manner over the temperature range of the pyrolysis method.

In general, in the electromagnetic spectrum, microwaves lie between infrared and radio frequencies. The wavelengths of microwaves are between 1 mm and 1 m with corresponding frequencies between 300 GHz and 300 MHz, respectively. The two most commonly used microwave frequencies are 915 MHz and 2.45 GHz. Microwave energy is derived from electrical energy with a conversion efficiency of for example approximately 85% for 915 MHz but only 50% for 2.45 GHz. Most of the domestic microwave ovens use the frequency of 2.45 GHZ. Compared with 2.45 GHz, the use of low frequency microwaves of 915 MHz can provide a substantially larger penetration depth which is an important parameter in the design of microwave cavity size, process scale up, and investigation of microwave absorption capacity of materials. Therefore, using low frequency microwaves enhances the efficiency of the pyrolysis method.

Further, the utilization of multiple small magnetrons for generating microwave radiation that are shut on and off for temperature control as known from the prior art are less efficient than a variable power low frequency microwave system as used in the pyrolysis method of the present invention. Radiation from a variable power low frequency microwave system allows for very good temperature control during the recovery of components from the carbon based material. Most of the pyrolitical oils, hydrocarbons, monomers and chemicals, including plasticizers, are very temperature sensitive resulting in yield and quality being affected negatively in the absence of good temperature control.

According to the present invention the pyrolysis method recovers an oil, a hydrocarbon, a monomer and/or a chemical plasticizer from the carbon based material. These components are extracted from the material by applying varied microwave power in various zones of the microwave reactor and the zones operate independently from each other. Microwave radiation used is in the range of 300 MHz to about 2.2 GHZ. The applied radiation power can be selected according to the decomposition temperature of a target recovery component. The power can be changed variably between different decomposition temperatures of differing target recovery components. Also, the variation in microwave power can adjust the speed of temperature change in the pyrolytic chamber. Thus, conditions in the chamber can be adapted to varying decomposition reactions of differing target recovery components.

Preferably, the carbon based material is a feedstock or waste material stream comprising plastics, rubber products, polymer composites or tires. Plastics comprises ethylene (co) polymer, propylene (co) polymer, styrene (co) polymer, butadiene (co) polymer, polyvinyl chloride, polyvinyl acetate, polycarbonate, polyethylene terephthalate, (meth) acrylic (co) polymer, or a mixture thereof. Rubber products and tires comprise of natural and synthetic rubbers such as styrene butadiene rubber and butyl rubber. These components of the plastics, rubber products and tires are recovered by the pyrolysis method.

Further, the microwave radiation for the pyrolysis method of the present invention is preferably selected from an VHF-Band, S-Band, UHF-Band and/or L-Band of the microwave spectrum. The radiation band is selected according to a range of variable power required for the pyrolysis method. For example, the radiation band can be selected according to a decomposition temperature to be applied. Also, more than one microwave radiation source can be used in the pyrolysis reactor, each radiating in a different radiation band.

Advantageously, the pyrolysis method of the present invention recovers at least one of the components of DL Limonene, isoprene, butadiene, benzene, toluene, o-xylene, m-xylene, p-xylene styrene and/or phthalates.

In one variant of the pyrolysis method according to the present invention the carbon based material is tempered in the pyrolytic chamber to around −4° C. to recover butadiene, to around 35° C. to recover isoprene, to around 80.1° C. to recover benzene, 110.6° C. to recover toluene, to around 138.3° C. to recover p-xylene, to around 139.1° to recover m-xylene, to around 144.4° C. to recover o-xylene, to around 145.2° C. to recover styrene, to around 178° C. to recover DL Limonene and/or to 300° C.-410° C. to recover phthalates. The indication of the temperatures being around these values shall be understood in that the temperature may deviate slightly from that value but not significantly enough to alter the recovery process of the respective component.

Pyrolytic oils are complex mixtures of different chemical components with a wide range of molecular weights and boiling points. It has been found that condensation fractions obtained by fractional condensation of pyrolytic oils, that are boiling between −4° C. and 600° C., contain commercially valuable chemicals.

According to one aspect of the pyrolysis method of the present invention a pyrolytic oil is subjected to a fractional condensation at temperatures ranging from −4° C. to 600° C. to recover at least on component thereof. Preferably, a component recovered from the pyrolytic oil is selected from the group consisting of paraffins, naphthenes, olefins and aromatics.

The fractional condensation process preferably comprises the steps of a fast extraction of volatiles for reducing volatile residence time in the pyrolytic chamber. Next, the volatile gasses are condensed into different fractional oil components. Optionally, the fractioned components are subjected to a further fractional condensation to isolate at least one commercially valuable chemical selected from the group consisting of paraffins, naphthenes, olefins and aromatics.

Particularly interesting components identified in the above condensation fractions are as mentioned above: butadiene recovered around −4° C., isoprene recovered around 35° C., benzene recovered around 80.1° C., toluene recovered around 110.6° C., p-xylene recovered 138.3° C., m-xylene recovered around 139.1°, o-xylene recovered 144.4° C., styrene recovered 145.2° C., DL Limonene recovered 178° C. and phthalates recovered between 300° C. and 410° C.

These components can be used as solvents and petrochemical feedstock in the synthesis of various polymers enabling resource circularity. For example, styrene is mainly used in the production of plastics, rubber and resins. Xylene is particularly useful in the production of polyester fibers; it is also used as solvent and starting material in the production of benzoic and isophthalic acids. Toluene is also used for the production of benzoic acid. DL Limonene is mainly used as a flavoring agent in the chemical, food and fragrance industries.

Thus, by utilizing the variable power, low frequency microwave process, under controlled atmosphere, and carrying out the fractional condensation of the pyrolytic oils to recover a fraction boiling in the range of about −4° C. to about 600° C., it is possible to recover the above commercially valuable chemicals.

The controlled atmosphere is advantageously a negative pressure environment applied in the pyrolytic chamber. Preferably, the pressure in the chamber is below 10 kPa.

Further, the controlled atmosphere can be realized as a reactive atmosphere to modify the component or products of components formed during decomposition. The controlled atmosphere is advantageously defined by at least one reactive gas, which may include hydrogen, steam, methane, benzene, or a mixture of reactive gases, such as for example contained in syngas. Advantageously, reactive gases, particularly syngas, formed during the pyrolysis method are partially recycled through the reactor to promote alternate reactions or increase the yield of target liquid or gas products.

Alternatively, an inert atmosphere to prevent oxidation during the pyrolysis process can be applied.

The controlled atmosphere in the pyrolytic chamber can be selected and adapted according a target component to be recovered by the pyrolysis method.

In the following one example of the pyrolysis method for recovering a component from carbon based material according to the present invention is described. As an example carbon based material vulcanized natural rubber is pyrolized. The vulcanized natural rubber was pyrolized by the variable power, low frequency microwave process under the following conditions: vacuum at 10 kPa; at 915 MHz in the L-Band; at a pyrolysis temperature of 350° C.-370° C.; fast extraction of volatiles; low reactor residence time to prevent secondary reactions. Volatiles were condensed using a fractional condensation process and yielded more than 33% DL Limonene amongst other chemicals. DL Limonene is notoriously sensitive to temperature degradation. The DL Limonene yield is high compared to existing processes such as disclosed in: Roy C., Darmstadt H., Benallal B., Amen-Chen C. "Characterization of naphtha and carbon black obtained by vacuum pyrolysis of polyisoprene rubber. Fuel Process." Technol. 1997; 50:87-103. doi: 10.1016/S0378-3820 (96) 01044-2. In this reference the DL Limonene yield was 16.6%.

Figure 2:
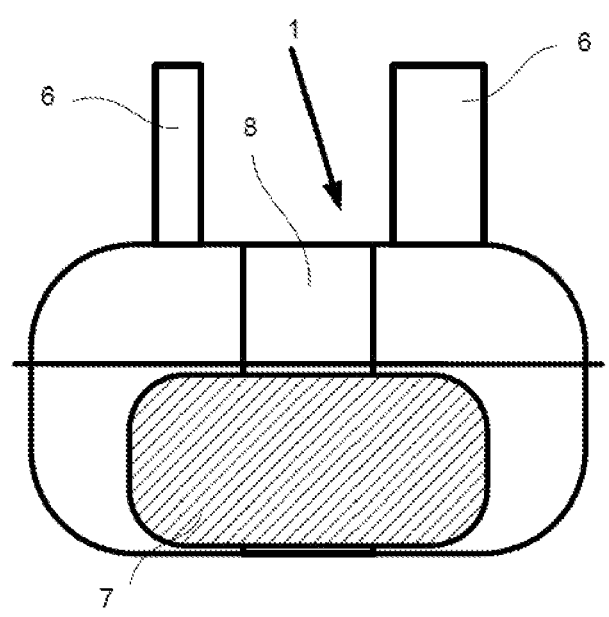

Example embodiments of the invention will be described in the accompanying drawings, which may explain the principles of the invention but shall not limit the scope of the invention or exclude other example embodiments. The drawings illustrate:

FIG. 1: a schematic diagram of a first example set up of a pyrolysis reactor according to the invention, and FIG. 2: a schematic view of a second example set describing a pyrolytic chamber of a pyrolysis reactor according to the invention.

In the following two example embodiments of a pyrolysis reactor according to the present invention are described which are suitable to perform a pyrolysis method for recovering at least one component from a carbon based material using thermal decomposition according to the invention. In both of the embodiments, the pyrolysis reactor for thermal decomposition of carbon based materials, particularly pyrolytic oils, hydrocarbons, monomers and chemicals from feedstock and waste streams such as tires, plastics, rubber products and polymer composites, comprises a pyrolytic chamber 1 for accommodating the carbon based material. Further, the example embodiments of the pyrolysis reactor comprise at least one microwave radiation source as a heat source for heating the carbon based material to a decomposition temperature of the carbon based material. A control unit is provided, which comprises a microwave radiation control for applying microwave radiation of variable power at frequencies between 300 MHz and 2200 MHZ to the carbon based material, and a temperature control for controlling a sequentially varying or increasing decomposition temperature of the carbon based material.

The two example embodiments mainly differ in the design of their pyrolytic chamber, while other features of the reactor and steps of the method are the same. Therefore, structural features of the reactor and explanations of method steps that are suitable for both example embodiments and shall be regarded as interchangeable between the two example embodiments.

For example, for both example embodiments it is advantageous to define that the temperature range of the pyrolysis method extends between -20° C. and 750° C., particularly between -4° C. and 600° C., and preferably does not exceed 750° C. The microwave radiation is advantageously selected from an VHF-Band, S-Band, UHF-Band and/or L-Band of the microwave spectrum. The example embodiments are suitable to pyrolyze a pyrolytic oil and subjected it to a fractional condensation at a temperature range between -4° C. and 600° C. The pyrolytic chamber may comprise a controlled atmosphere in form of a negative pressure environment, particularly a pressure below 10 kPa, or the controlled atmosphere is defined by at least one reactive gas, particularly a gas selected from hydrogen, steam, methane, benzene or a mixture thereof. The example embodiment allow for the extraction of volatile gasses from the pyrolytic chamber and condensing the gasses into different fractional oils. In the same way other features and steps apply to both of the embodiments.

FIG. 1 shows an example embodiment of the a pyrolytic reactor in the form of a continuous flow retort with an elongated design. For example, it may comprise a conveyor to deliver carbon based material to the pyrolytic chamber 1 and transfer the material and decomposed components thereof through the pyrolytic chamber 1.

For example, complete tyres, plastics, rubber products and polymer composites can intermittently be fed into the pyrolytic chamber 1 from a first end of the chamber. An air lock system with means for purging of oxygen can be provided at the first end.

Pyrolysis gases are drawn off at intervals along the length of the pyrolytic chamber 1, wherein successive exit ports 2 are provided at points of increasing product temperature and different gases or compounds can be collected. In the variant of FIG. 1, gases are collected from exit ports 2a, 2b and 2c at three positions on the side of the chamber, that correspond to three different recovery components. Solid products may be discharged through an airlock system at an end of the pyrolytic chamber 1 and may be separated using a suitable method, such as a vibrating screen 5 or the like.

A process control unit, such as a programmable logic controller (PLC), is used to control the pyrolysis process according to the invention. The control unit comprises a microwave radiation control for applying microwave radiation of variable power at frequencies between 300 MHz and 2200 MHZ to the carbon based material and a temperature control controlling a sequentially increasing decomposition temperature of the carbon based material. Also, the control unit can control the temperature at various successive heat zones 10 along the pyrolytic chamber 1.

In the example pyrolysis reactor shown in FIG. 1 carbon based material is introduced into a first end of the pyrolytic chamber 1 by a conveyor and transported along the length of the pyrolytic chamber 1. In the course of the sequentially increasing decomposition temperature the pyrolytic chamber and the carbon based material respectively are first heated to a first decomposition temperature of a first component of the carbon based material within a first heat zone, by a low frequency variable power microwave radiation. First products may be evacuated through a first exit port 2a. In the example having three heat zones shown in FIG. 1, the temperature in the first heat zone 10a is for example around 35° C. to recover isoprene, the temperature in the second heat zone 10b is for example around 110.6° C. to recover toluene, and the temperature in the third heat zone 10c is for example around 145.2° C. to recover styrene.

The pyrolytic chamber 1 can be designed as a continuous reactor and the subsequent heat zones can merge into each other.

At a second end of the pyrolytic chamber 1 further recovery components or feedstock remnants my be discharged through the airlock system.

FIG. 2 shows a schematic view of a pyrolytic chamber 1 of a second example embodiment of the pyrolysis reactor according to the present invention. The reactor has the form of a batch reactor such as a pressure vessel that opens to accept a load of carbon based material such as tyres. For example, the pyrolytic chamber 1 of the reactor is of circular shape and may be opened at the top of the circular chamber.

In the shown example embodiment the reactor is loaded with a single tyre 7. Microwave radiation is applied to the pyrolytic chamber 1 through feed ports 6 in a roof of the chamber. Electrical elements or burning off of some of the pyrolysis products may provide heating of the chamber walls to assist with heating and to prevent condensation inside the vessel. The variable power, low frequency microwave power is introduced through a number of microwave feed ports 6 on the roof of the vessel that are arranged in positions and orientations that ensure a uniform distribution of microwave radiation in the chamber 1. The chamber may also be in the shape of an annulus where the central portion 8 is removed to reduce unoccupied volume in the pyrolytic chamber 1.

In the batch reactor the temperature of the carbon based material can be increased in heating steps to the decomposition temperature differing components to be recovered. Condensate can be collected in a storage dedicated to that component, switching between condensate storages for each step of the sequential pyrolysis process. During the process the reactor wall temperature can also be increased in heating steps to prevent re-condensation of the volatiles in the reactor. The temperature can be controlled by the control unit. In each heating step recovery components are extracted from the pyrolytic chamber 1 through the exit port 2 and can enter a condenser system.

The pyrolysis method and the pyrolysis reactor according to the present invention relies on the fact that each of the material components present in a carbon based material has different boiling points and microwave absorption properties. The application of variable power microwave radiation at frequencies between 300 MHz and 2200 MHZ, i.e. low frequency microwaves, to sequentially increase the temperature in the pyrolytic chamber over a temperature range including the decomposition temperature of recovery component ensures a high yield of recovery and high quality of the recovered components.

LIST OF REFERENCE NUMBERS

1 pyrolytic chamber
2a, b, c exit ports
5 vibrating screen
6 feed port
7 rubber tyre
8 centre portion
10a, b, c heat zones It is claimed:

1. A pyrolysis method for recovering at least one component from a carbon based material using thermal decomposition, comprising the steps of:
    delivering the carbon based material to a pyrolytic chamber, and exposing the carbon based material to a controlled atmosphere and heating to a decomposition temperature of the at least one component in the pyrolytic chamber by microwave radiation,
    applying a variable power microwave radiation at frequencies between 300 MHz and 2200 MHZ to vary a temperature in the pyrolytic chamber sequentially over a temperature range including the decomposition temperature of the at least one component.

2. The pyrolysis method according to claim 1, wherein the temperature range does not exceed 750° C.

3. The pyrolysis method according to claim 1, wherein the temperature range extends between −20° C. and 750° C.

4. The pyrolysis method according to claim 1, wherein the carbon based material is a feedstock or waste material stream comprising plastics, rubber products, polymer composites and/or tires.

5. The pyrolysis method according to claim 1, wherein the microwave radiation is selected from an VHF-Band, S-Band, UHF-Band and/or L-Band of the microwave spectrum.

6. The pyrolysis method according to claim 1, wherein the at least one recovered component is an oil, a hydrocarbon, a monomer and/or a chemical plasticizer.

7. The pyrolysis method according to claim 1, wherein the at least one recovered component is DL Limonene, isoprene, butadiene, benzene, toluene, o-xylene, m-xylene, p-xylene styrene and/or phthalates.

8. The pyrolysis method according to claim 7, wherein the carbon based material is tempered to around −4° C. to recover butadiene, to around 35° C. to recover isoprene, to around 80.1° C. to recover benzene, 110.6° C. to recover toluene, to around 138.3° C. to recover p-xylene, to around 139.1° to recover m-xylene, to around 144.4° C. to recover o-xylene, to around 145.2° C. to recover styrene, to around 178° C. to recover DL Limonene and/or to 300° C.-410° C. to recover phthalates.

9. The pyrolysis method according to claim 1, wherein the at least one recovered component is a pyrolytic oil that is subjected to a fractional condensation at a temperature range between −4° C. and 600° C.

10. The pyrolysis method according to claim 9, wherein the recovered pyrolytic oil is selected from the group consisting of paraffins, naphthenes, olefins and aromatics.

11. The pyrolysis method according to claim 1, wherein the controlled atmosphere is a negative pressure environment applied in the pyrolytic chamber.

12. The pyrolysis method of claim 11, wherein the pressure is below 10 kPa.

13. The pyrolysis method according to claim 1, wherein the controlled atmosphere is defined by at least one reactive gas.

14. The pyrolysis method of claim 13, wherein the gas is selected from hydrogen, steam, methane, benzene or a mixture thereof.

15. The pyrolysis method according to claim 1, wherein volatile gasses are extracted from the pyrolytic chamber and are condensed into different fractional oils.

16. The pyrolysis method according to claim 15, wherein at least one of the different fractional oils is subjected to a further condensation to isolate at least one of the group consisting of paraffins, naphthenes, olefins and aromatics.

17. The pyrolysis method of claim 1, wherein the temperature range extends between −4° C. and 600° C.

* * * * *